United States Patent
Matsuda et al.

(10) Patent No.: US 7,771,714 B2
(45) Date of Patent: Aug. 10, 2010

(54) MEDIUM COMPRISING CHICKEN LEUKEMIA INHIBITORY FACTOR (LIF)

(75) Inventors: Haruo Matsuda, Hiroshima (JP); Shuichi Furusawa, Hiroshima (JP); Hiroyuki Horiuchi, Hiroshima (JP)

(73) Assignee: Hiroshima University, Hiroshima (JP)

( * ) Notice: Subject to any disclaimer, the term of this patent is extended or adjusted under 35 U.S.C. 154(b) by 151 days.

(21) Appl. No.: 11/826,581

(22) Filed: Jul. 17, 2007

(65) Prior Publication Data
US 2009/0029458 A1    Jan. 29, 2009

Related U.S. Application Data

(62) Division of application No. 11/102,749, filed on Apr. 11, 2005, now Pat. No. 7,250,275, which is a division of application No. 10/061,375, filed on Feb. 4, 2002, now Pat. No. 7,029,664.

(30) Foreign Application Priority Data
Jun. 7, 2001 (JP) .............................. 2001-171993

(51) Int. Cl.
*A61K 38/20* (2006.01)
(52) U.S. Cl. .............................. 424/85.2; 514/2; 514/8; 514/12; 514/885
(58) Field of Classification Search ........................ None
See application file for complete search history.

(56) References Cited

U.S. PATENT DOCUMENTS
4,064,007 A * 12/1977 Choay et al. ................ 424/115

OTHER PUBLICATIONS

Mikayama et al. (1993), Proc. Natl. Acad. Sci. USA vol. 90, pp. 10056-10060.*
Voet et al. (1990), Biochemistry John Wiley & Sons, Inc., pp. 126-128 and 228-234.*
Isobe et al. (1984), J. of Protozoology, 31(1), pp. 186-187.*
Fayon et al. (2006) Am J. Physiol Lung Cell Mol Physiol 291:244-251.*
Callard and Gearing (1994). The Cytokine Factsbook, Academic Press, p. 163.*

* cited by examiner

*Primary Examiner*—Prema Mertz
(74) *Attorney, Agent, or Firm*—Westerman, Hattori, Daniels & Adrian, LLP

(57) ABSTRACT

The present invention is to provide a chicken LIF gene. Based on this genetic information, LIF protein derived from the chicken can be stably supplied and it solves the problems of the creation of transgenic chickens in the past. In addition, the present invention provides not only transgenic chickens for testing purposes but also supplies the first practical transgenic stock animals. The present invention relates to leukemia inhibitory factor (LIF) shown in sequence No. 2, and the gene that encodes thereof shown in sequence No. 1, and a manufacturing method of chicken LIF. In addition, the present invention pertains to a differential preventer of the chicken differentiable cell, and a method of chicken differential prevention and a culturing method for the chicken differentiable cell using thereof, and a medium comprising thereof.

2 Claims, 6 Drawing Sheets

```
  1  GCGGGGGAACATGAATTTCTGAAAACCCTCACACGCCGCCCGTCTGCGCTCGGCTCTCCG

61  GGACGGCGCTCACCATGAGGCTCATCCCCGCAGGTGTCGTGCCCTTCGTGGCCCTGCTGC   120
                   M  R  L  I  P  A  G  V  V  P  F  V  A  L  L

121  TGCTGCAGAGGAGGCCGGTGTCCGGGCGGGCGCTGCTGGGGACGAGCTCTGCGTGTCCCA   180
      L  Q  R  R  P  V  S  G  R  A  L  L  G  T  S  S  A  C  P  T

181  CCAACGGGCTGTGCCGGGCCAATGTCCTGGAGCAGACCCGCAGGCAGGTCGCACTGCTCA   240
      N  G  L  C  R  A  N  V  L  E  Q  T  R  R  Q  V  A  L  L  N

241  ACGCCACCGCGCAGGACCTCTTCAGCCTCTACTTGAAGTGCCAGGGAGAGCCGTTCAGCA   300
      A  T  A  Q  D  L  F  S  L  Y  L  K  C  Q  G  E  P  F  S  S

301  GCGAGAGCGACCGCCTCTGCAGCCCCAGTGGCATCTTCTTCCCCCCCTTCCACGTCAACC   360
      E  S  D  R  L  C  S  P  S  G  I  F  F  P  P  F  H  V  N  R

361  GGACCACCGAGAGGAAGGAGGTGATGGTGGCCATGTACAAGCTCTTCGCCTTCCTCAACG   420
      T  T  E  R  K  E  V  M  V  A  M  Y  K  L  F  A  F  L  N  A

421  CCTCACTGGGGAACATCACCCGCGACCAGGAGGAGCTCAACCCCATGGCCAAGGAGCTCC   480
      S  L  G  N  I  T  R  D  Q  E  E  L  N  P  M  A  K  E  L  L

481  TCAACCGCCTCCACAACACCACCAAAACCACGCGGGGCCTCATCTCCAACCTCACCTGCC   540
      N  R  L  H  N  T  T  K  T  T  R  G  L  I  S  N  L  T  C  L

541  TGCTCTGCAAGCACTACAACATCTTCCAGGTGGACGTGAGCTACGGGGAGAGCAGCAAGG   600
      L  C  K  H  Y  N  I  F  Q  V  D  V  S  Y  G  E  S  S  K  D

601  ACAAGAGCGCCTTCAAGAAGAAGCAGCAGGGCTGCCAGGTGCTCAGGAAGTACGTGCAGG   660
      K  S  A  F  K  K  K  Q  Q  G  C  Q  V  L  R  K  Y  V  Q  V

661  TCATCGCCCAGGCTGCTCGTGTCCTCCTACCTCACCTCAGCCCCGCGTGAGCCCCGGCCC   720
      I  A  Q  A  A  R  V  L  L  P  H  L  S  P  A  *

721  CCGCGCCACGCTACCACCGGGACAGCGGACATCTCCTTGCACCCGTCTCAGAGATGGGCA   780

781  CGGCGAGGC   789
```

|  |  |  |  |
|---|---|---|---|
| CHICKEN | 1 | MRLIPAGVVPFVALILQRRPVSGRAF-LG-TSSAPTNGLCRANVLEDTRRQVALNAT | 58 |
| HUMAN | 1 | MKVLAAGVVP-FLLLVLHWKHGAGSPLPITPVNATCAIRHPCHNNLMNQIRSQLAQLNGS | 58 |
| MOUSE | 1 | MKVLAAGIVPLL-LLVLHWKHGAGSPLPITPVNATCAIRHPCHGNLMNQIKNQLAQLNGS | 59 |
| CHICKEN | 59 | AQDFSYLKCQGEPFSSESDRLCSPSGIFFPPFHVNRTTERKEVMAMKLFAFENASL | 118 |
| HUMAN | 59 | ANALFILYYTAQGEPFPNNLDKLCGPNVTDFPPFHAN-GTE-KAKLVELYRIVVFLGTSL | 116 |
| MOUSE | 60 | ANALFISYTAQGEPFPNNVEKLCAPNMTDFPSFHGN-GTE-KTKLVELYRMVAYLSASL | 117 |
| CHICKEN | 119 | GNITRDQEELNPMAKEFLNRFHNTTKTTRGLISNLTCLCKHVNIFQVDVSYGESSKDKS | 178 |
| HUMAN | 117 | GNITRDQKILNPSALSLHSKLNATADILRGLLSNVLCRLCSKYHVGHVDTYGPDTSGKD | 176 |
| MOUSE | 118 | TNITRDQKVLNPTAVSLQVKLNATIDVMRGLLSNVLCRLCNKYRVGHVDVPPVPDHSDKE | 177 |
| CHICKEN | 179 | AFKKQQGCQVERKYVQVIAQAARVLLPHLSPA | 211 |
| HUMAN | 177 | VFQKKKLGCQLLGKYKQIIAVLAQAF------ | 202 |
| MOUSE | 178 | AFQRKKLGCQLLGTVKQVISMVQAF------ | 203 |

SIGNAL SEQUENCE

FORWARD PRIMER : AGAGCCGTTCAGCAGCGAGAGC
REVERSE PRIMER : GCCTCGCCGTGCCCATCTCTGA

◄ 502 bp

US 7,771,714 B2

MEDIUM COMPRISING CHICKEN LEUKEMIA INHIBITORY FACTOR (LIF)

RELATED APPLICATIONS

This application is a divisional of patent application Ser. No. 11/102,749, filed on Apr. 11, 2005, now U.S. Pat. No. 7,250,275 which is a divisional of patent application Ser. No. 10/061,375, filed on Feb. 4, 2002, now U.S. Pat. No. 7,029,664 the entire contents of which are incorporated herein by reference.

FIELD OF TECHNOLOGY

The present invention relates to a chicken leukemia inhibitory factor (hereinafter referred to as "LIF") and the gene thereof, as well as its manufacturing method. The chicken LIF of the present invention has a differentiation prevention function for a chicken differentiable cell such as a chicken's embryonic stem cell or embryonic reproductive cell, and is effective as an anti-differentiator while the chicken differentiable cell is being cultured.

The present invention also relates to a culturing method for a chicken differentiable cell using a chicken LIF, a culture medium, and a creation method for a transgenic chicken using said method, and a transgenic chicken created with said method.

BACKGROUND OF THE INVENTION

Recently, the creation of transgenic animals has brought significant progress in a wide range of areas including medicine and biology. The creation of animals that are introduced with specific genes or knocked-out specific genes has become an important tool to analyze the functions of these genes. There have been two types of creation methods for transgenic animals: the transgenic method in which a foreign gene is directly introduced to a fertilized egg, and the gene introduction method that is carried out via an embryonic stem cell (hereinafter referred to as an ES cell). Currently, the introduction of a gene to the ES cell has been widely used because the target gene can be introduced or there is a knock-out from a designated genome location using the gene targeting method.

As described above, the creation of transgenic animals using the ES cell by the gene targeting method has been widely carried out. In this method, the inhibition of the differentiation during the engineering of the gene is the significant issue. To culture an ES cell, the preparation of a feeder cell or the use of an LIF as a factor to inhibit the differentiation is required. The LIF is a type of cytokine that belongs to the IL-6 family. It is an essential material to maintain the cell in an undifferentiated state (Smith A., et al., Nature, 336, 688-690 (1988)).

A mouse LIF is an essential factor to create a transgenic mouse through the gene targeting method, and the recombinant LIF derived from the mouse has been commercialized. The culturing of a mouse ES cell has been realized using this factor only, however, the LIF has not been established for other animals and the creation of a transgenic animal using the gene targeting method has been difficult.

The creation of transgenic chickens has been attempted because its egg has a high productivity of proteins. The fertilized egg of the chicken is relatively easy to handle so that the introduction of genes has few problems. However, in order to introduce a knock-out of the gene to or from the designated location, the creation of a transgenic chicken using the gene targeting method is necessary.

Chickens and mice have different development patterns so that the ES cell cannot be used. However, it is possible to separate and culture a cell equivalent to the ES cell from the developing embryo of a chicken. Chickens have blastodermic cells and primordial reproductive cells that are equivalent to a mouse ES cell. Blastodermic cells are developing reproductive cells that are equivalent to the mouse ES cell. The primordial reproductive cell is a cell that is going to be differentiated to be a reproductive cell, and the development of a stock cell that can be externally cultured has advanced. This stock cell is called an embryonic germ cell. The issue is how to perform the culturing while maintaining the undifferentiated state for either cell. In any event, currently no chicken LIF has been found so that a medium that is a combination of another mammal LIF and another cytokine has been used. For example, a study has been carried out to establish a culturing system for chicken ES cells and embryonic reproductive cells using a recombinant LIF derived from a mouse. However, its effect is low and currently no culturing system has been established.

The chicken embryo is easy to obtain and the operation for the embryo is simple so that it has been widely used as a study material in embryology. In addition, the establishment of a production technology for transgenic chickens has been desired because chickens are not only used for their meat but also they have a high productivity of protein in their eggs, and are industrially important. However, a culturing system for the chicken ES cell and embryonic reproductive cell has not been established so that we have not reached the level where an artificial modification of the gene can be easily carried out (at the level of the transgenic mouse). Thus, the gene/protein cloning of chicken LIF, which is an essential factor for the culturing system is being quickened. Nevertheless, chickens are significantly different from other mammals and even the fact as to whether an LIF exists or not has not been determined. As described above, the manufacturing of chicken LIF protein has been desired in order to create transgenic chickens.

SUMMARY OF THE INVENTION

The present invention has taken advantage of state-of-the-art molecular biological techniques in order to solve these problems and to provide a gene for a chicken LIF. If a stable supply of the LIF protein derived from chickens is possible based on this genetic information, the problem of the creation of a transgenic chicken in the past can be resolved.

In addition, the present invention mass produces the recombinant LIF protein based on the genetic information of the present invention, and a supply thereof as the medium reagent for the chicken ES cell and embryonic reproductive cell in order to create a transgenic chicken. Consequently, it allows the providing of not only transgenic chickens for test purposes but also the first practical transgenic stock animals.

The present invention relates to a chicken LIF, and the gene that encodes thereof, and a manufacturing method for chicken LIF.

The present invention also relates to a differential preventer of a chicken differentiable cells comprising the chicken LIF, the differentiation prevention method of the chicken using thereof, a culturing method for the chicken differentiable cells, and the medium comprising thereof.

The present invention further relates to a method of creating transgenic chickens in which said differentiable cell is cultured in the presence of a chicken LIF, and the transgenic chicken that is created using said method.

The inventors of the present invention stimulated chicken monocytic cell stock (IN24) with a lipopolysaccharide (LPS), and using the subtraction method, the gene that excessively developed due to the LPS stimulation, was cloned. Additionally, a clone that is homological (approximately 30%) to the LIF derived from a mammal was obtained among these clones.

The cDNA base sequence of the obtained clone is shown in sequence No. 1 in the sequence table. This gene is comprised of 789 bases and it is assumed that it encodes the protein comprising 211 amino acids having an interpretation area of 75th atg to 708th tga.

The sequence of chicken LIF that is comprised of the assumed 211 amino acids is shown in sequence No. 2 in the sequence table. The one letter code of the amino acid of this amino acid sequence is shown as follows.

```
MRLIPAGVVP  FVALLLLQRR  PVSGRALLGT          30

SSACPTNGLC  RANVLEQTRR  QVALLNATAQ          60

DLFSLYLKCQ  GEPFSSESDR  LCSPSGIFFP          90

PFHVNRTTER  KEVMVAMYKL  FAFLNASLGN         120

ITRDQEELNP  MAKELLNRLH  NTTKTTRGLI         150

SNLTCLLCKH  YNIFQVDVSY  GESSKDKSAF         180

KKKQQGCQVL  RKYVQVIAQA  ARVLLPHLSP         210

A                                          211
```

In addition, the base sequence and amino acid (one letter code) of the obtained chicken LIF gene is shown in FIG. 1.

A comparison of the amino acid sequence assumed from the base sequence of the chicken LIF of the present invention with the amino acid sequence of the human LIF and mouse LIF is shown in FIG. 2. The black triangle in FIG. 2 shows the location of the cysteine and the white triangle shows the location where a saccharide can be added.

The amino acid sequence assumed from the base sequence of the chicken LIF of the present invention is homologous for less than 40% with the mouse LIF. Only a partial effect has been recognized with the culture system of the chicken ES cell and embryonic reproductive cell using the recombinant mouse LIF. This supports the fact that the mouse LIF and chicken LIF have a low homologue. However, the location of the cysteine, which is an important amino acid that determines the structure of protein, was completely identical among the chicken, human and mouse.

BRIEF DESCRIPTION OF DRAWINGS

FIG. 1 shows a chicken amino acid sequence and the DNA base sequence of the present invention.

FIG. 2 shows a comparison of the chicken LIF amino acid sequence with the human LIF and mouse LIF thereof.

PREFERRED EMBODIMENTS OF THE INVENTION

Figure 3:
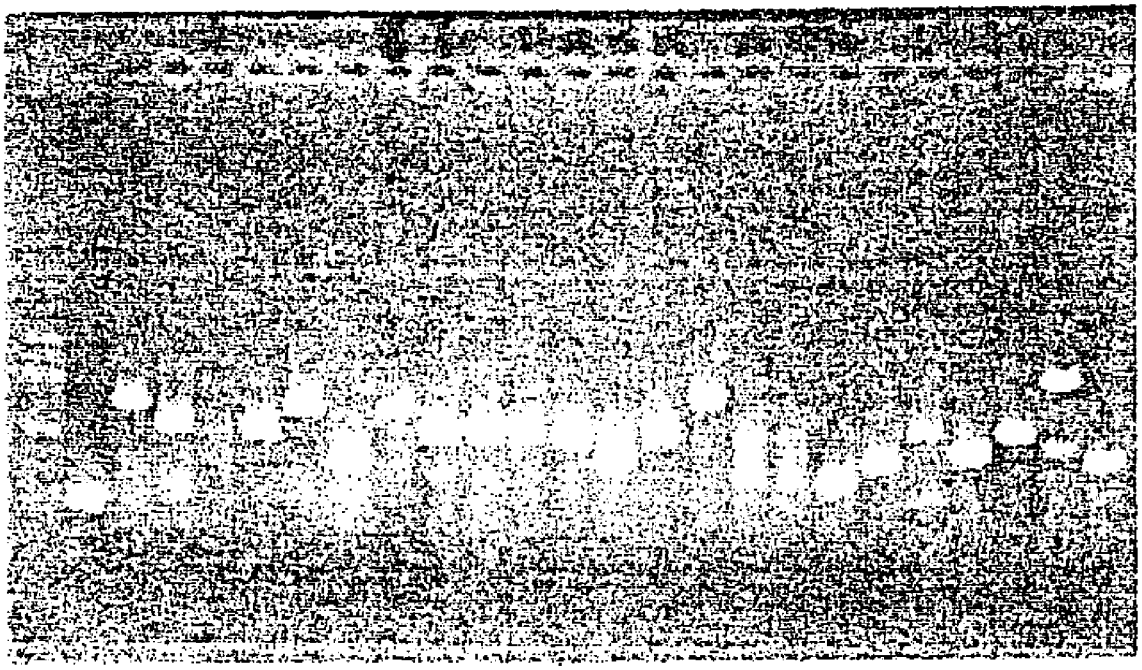
FIG. 3 is a photo in place of a drawing that shows a selected clone from the clones obtained by the subtraction method.

The chicken LIF of the present invention is not limited to the one having the amino acid sequence shown in sequence No. 2 in the sequence table. As long as it is LIF active for a chicken, a portion of the amino acid shown in sequence No. 2 can be deleted, or substituted with another amino acid, and/or added with another amino acid.

There is no particular limitation on the number of amino acids for deletion, substitution or addition, however it is preferable for it to be half or less, which is 1 to 100 or 1 to 50 pieces.

The chicken LIF gene of the present invention is not limited to those of them that have the base sequence shown in sequence No. 1 of the sequence table. As long as it encodes the protein that is LIF active for the chicken as described above, a portion of the amino acid shown in sequence No. 1 can be deleted, or substituted with another amino acid, and/or added with another amino acid. In addition, the chicken LIF gene of the present invention can be a double strand DNA or single strand DNA or RNA. Those of them that have a supplemental base for said chicken LIF of the present invention are included in the chicken LIF gene of the present invention. Furthermore, the chicken LIF gene of the present invention includes a base sequence that can be hybridized under stringent conditions.

In addition, the present invention provides a fragment of a chicken LIF gene of the present invention. The fragment of the chicken LIF gene of the present invention can be used as a probe to detect, identify or quantify the chicken LIF gene of the present invention, and as a primer in order to obtain the chicken LIF gene of the present invention.

As a fragment of the chicken LIF gene of the present invention, approximately 5 to 50 bases, 5 to 30 bases or 10 to 30 bases of the sequence from an arbitrary location can be used.

The manufacturing method of the chicken LIF of the present invention can be carried out using a well-known method using said chicken LIF gene of the present invention. For example, a gene that has the base sequence shown in sequence No. 1 is combined into a manifestation vector and a phenotypic transformation of the host cell is carried out. Additionally, it can be manufactured through the culturing of the phenotypically transformed host cell. A prokaryotic cell such as *E. coli* or an eukaryotic cell such as a cell from yeast or a mouse can be used as the host cell.

Based on the chicken LIF gene of the present invention, a recombinant chicken LIF can be created using a prokaryotic cell or a eukaryotic cell, and consequently, the mass production of the chicken LIF necessary to create a transgenic chicken can be realized.

Examples of the chicken differentiable cell of the present invention are, chicken ES cells and embryonic reproductive cells.

When a chicken differentiable cell is cultured, the chicken LIF of the present invention can prevent the differentiation of said cell by being added in the culture system. Therefore the chicken LIF of the present invention can be used as the differentiation preventer of the chicken differentiable cell. Purified chicken LIF of the present invention can be individually used as the differentiation preventer of the present invention or it can be used in a mix with a carrier. More over, a medium to culture the chicken differentiable cells can be created by mixing the LIF of the present invention with the medium in advance.

Furthermore, the present invention provides a culturing method for the chicken differentiable cells using the LIF of the present invention. It provides a culturing method for a chicken differentiable cells by adding said differentiation preventer of the present invention into the culture system, or using said medium of the invention.

In addition, the present invention provides a creation method for a transgenic chicken and a transgenic chicken created using the method hereof. An example of the desirable creation method of the transgenic chicken of the present invention is such that the differentiable cells such as the chicken ES cells and embryonic reproductive cells with modified genetic information are modified and cultured thereof: preferably by introducing a foreign gene that can be developed at a specific genome location through a gene targeting method; or through a modification in order to inhibit the development of a specific gene at specific genome locations, for instance, an introduction of a foreign gene to destroy an Exon area such as a promoter area or a modification of the gene to modify or add encoded amino acid. When chicken ES cells or embryonic reproductive cells are used as the differentiable cells, normally, a chimera chicken is obtained. Additionally, the next generation thereof becomes a transgenic chicken in which the target gene is introduced or knocked out.

The recombinant chicken LIF created based on the chicken LIF gene of the present invention is a discovery with hope in order to provide an established method for to the creation of transgenic chickens. The use of this allows the maintenance of the subculture of the chicken ES cells and embryonic reproductive cells in an undifferentiated state, which has been impossible in the past, and also allows the in-vitro selection of the introduced gene, which has been difficult for chickens. In other words, all the problems regarding the creation of a transgenic chicken have been resolved with the present invention.

In addition, when the culture system of these cells is established, the creation of a transgenic chicken will become even simpler than a mouse, allowing the poultry industry to produce (produced as eggs) utility materials (medical drugs, reagents for clinical tests, etc.).

Embodiments

The present invention is described in detail using embodiments as follows, however, the present invention is not limited to these embodiments.

Embodiment 1

Gene Cloning of the Chicken LIF mRNA was purified from chicken monocytic cell stock (IN24) stimulated with a lipopolysaccharide (LPS) and not stimulated separately, and then double strand cDNA was synthesized.

Using the cDNA obtained from these two types of cells, a subtraction method was carried out using the Clontech PCR-select cDNA subtraction kit. The cDNA obtained was cloned to the pGEM-T vector. These clones were phenotypically transformed to JM109 *E. coli* and cultured on an agar medium and then the developed colony was selected using the PCR method. It was selected such that the PCR was carried out using the pUC-M13 forward primer and reverse primer in the pGEM-T vector base sequence and only those clones with cDNA inserted in the vector were selected. The results are shown in FIG. 3 as a photo in place of a drawing.

Finally, 122 clones were selected and the plasmid of these clones was created. Then using an auto-sequencer, the base sequence of each clone was determined.

Each of the determined base sequences were checked against a database, and then it was found that one of the clones is a clone that is homologous with a mammalian (cows, pigs, etc.) derived LIF.

As described above, we determined that the obtained clone is a part of the gene (259 bp) that encodes the chicken LIF. Based on this base sequence of the clone, the cloning of the complete chicken LIF was carried out by the RACE method using the Clontech smart-RACE kit.

Figure 4:
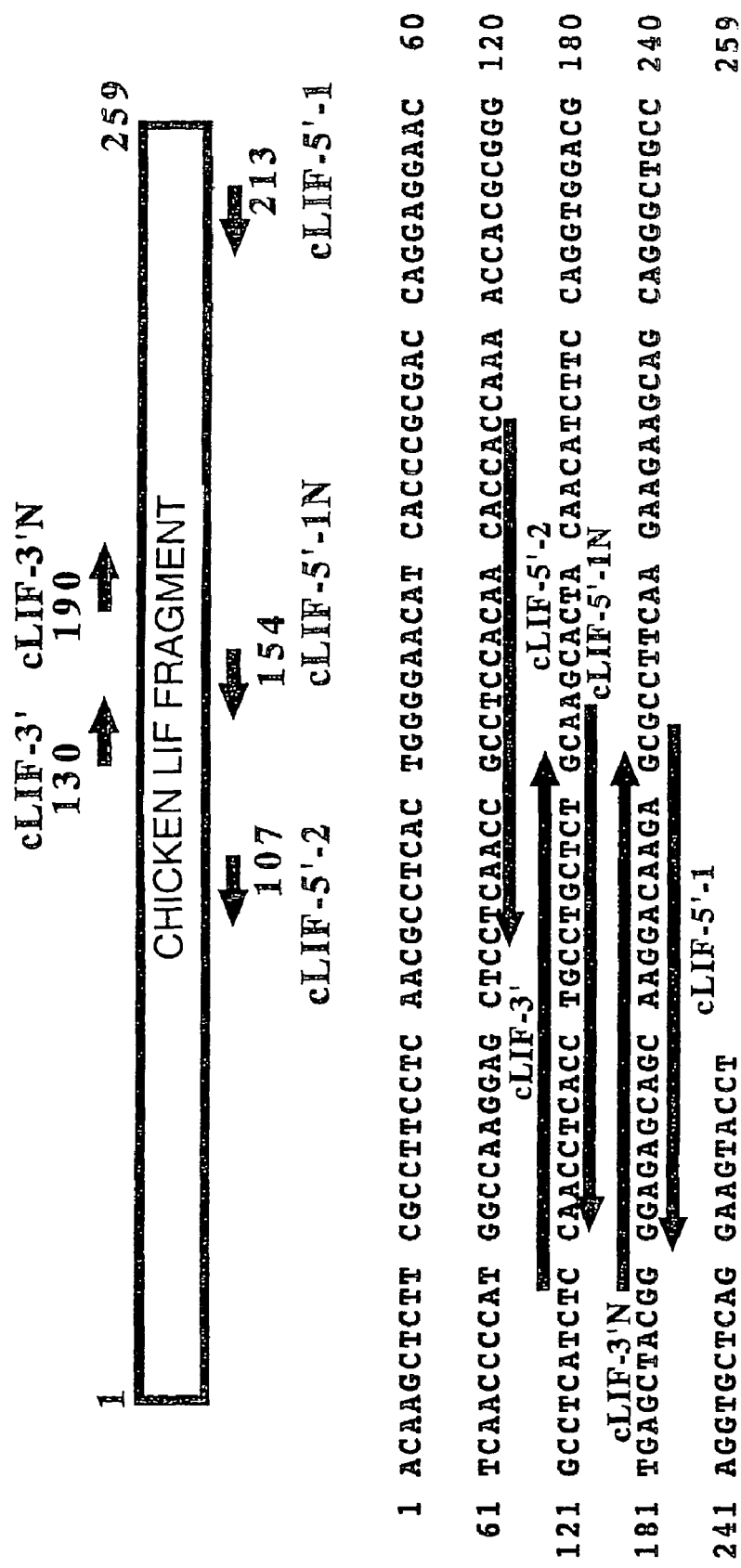
FIG. 4 shows the location of the primer and its sequence when the RACE method is applied to the clones obtained by the subtraction method.

Based on the obtained chicken LIF gene base sequence, at the location shown in FIG. 4, primers for 3' and 5' were prepared and a PCR was carried out between the adaptor sequences. The top line of FIG. 4 is a schematic view of the 259 bp sequence obtained as above, and the bottom line shows its specific sequence.

As a result, 789 bp was determined including the entire translated area.

Figure 5:
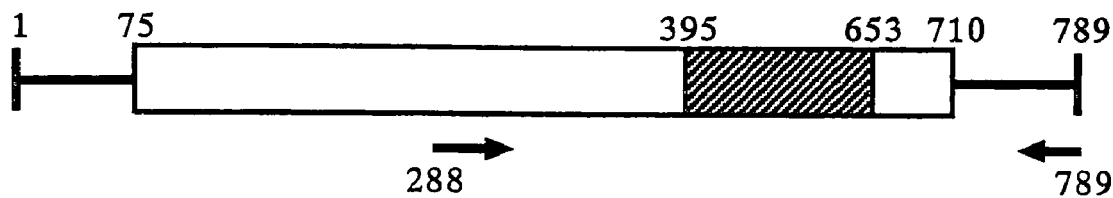
FIG. 5 shows the schematic structure of a cDNA base sequence of a chicken LIF of the present invention. The arrow shows the location of the primer of the RT-PCR method that was carried out in order to confirm the sequence.

The determined base sequence was confirmed from the fragment obtained through the RT-PCR method using the new primer shown in FIG. 5. The square-framed portion in FIG. 5 shows the translated area and the shadowed portion shows the 259 bp portion obtained through said subtraction method. The arrow in the bottom line in FIG. 5 shows the primer portion of the RT-PCR.

Figure 6:
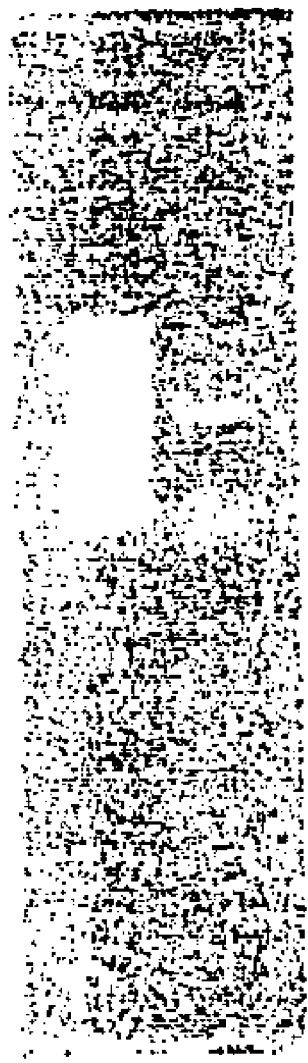
FIG. 6 is a photo in place of a drawing that shows the results of a 502 bp fragment obtained by the RT-PCR method.

The results of electrophoresis of the 502 bp fragment amplified by the RT-PCR method are shown in FIG. 6 as a photo in place of a drawing. The lane M indicates the marker and the black triangle shows the location of the 502 bp fragment.

The base sequence and amino acid (one letter code) of the obtained chicken LIF gene is shown in FIG. 1. Its base sequence is shown in sequence No. 1 and the amino acid sequence is shown in sequence No. 2.

The present invention is to provide a chicken LIF and the gene thereof that is necessary to create a chicken with introduced foreign genes (transgenic chicken) for the first time. The present invention is on the frontier of the creation of a chicken with introduced foreign genes (transgenic chicken) and in addition, it is expected to lead to the mass production of utility materials such as medical drugs. So far, the progress of studies and the practical use of the creation of a transgenic chicken have been extremely delayed because a chicken LIF has been unknown, however, the providing of the chicken LIF of the present invention allows practical use to the same extent as that for a mouse.

It is easy to obtain the embryo of a chicken and it has good operability. The chicken LIF of the present invention allows the establishment of a culturing system of chicken ES cells, allowing the creation of transgenic chickens, which is even easier than that for a mouse. This is not just at the laboratory level but also it allows the application to breeding in the poultry industry. In addition, because the chicken egg has a high productivity of protein, it allows the practical manufacturing of utility materials (medical drugs, clinical test reagents, etc.). The present invention opens up the road for the first time to a supply of practical level transgenic stock animals.

The disclosure of Japanese Patent Application No. 2001-171993 filed Jun. 7, 2001 including specification, drawings and claims are herein incorporated by reference in their entirety.

Although only some exemplary embodiments of this invention have been described in detail above, those skilled in the art will readily appreciated that many modifications are possible in the exemplary embodiments without materially departing from the novel teachings and advantages of this invention. Accordingly, all such modifications are intended to be included within the scope of this invention.

We claim:

1. A chicken differentiable cell culture medium, comprising:
    a purified chicken leukemia inhibitory factor (LIF), said chicken leukemia inhibitory factor (LIF) comprising the amino acid sequence of SEQ ID NO: 2,
    wherein said chicken differentiable cell culture medium is produced by mixing said purified chicken leukemia inhibitory factor (LIF) with a medium, and wherein said chicken differentiable cell culture medium is produced by transforming a host cell with a vector comprising a nucleic acid sequence encoding the amino acid sequence of SEQ ID NO: 2, producing the chicken LIF, and recovering the chicken LIF from the host cell, prior to mixing said purified chicken LIF with said medium.

2. The chicken differentiable cell culture medium in accordance with claim 1, wherein the chicken differentiable cell is a chicken embryonic stem cell or an embryonic germ cell.

* * * * *

SEQUENCE LISTING

```
<160> NUMBER OF SEQ ID NOS: 7

<210> SEQ ID NO 1
<211> LENGTH: 789
<212> TYPE: DNA
<213> ORGANISM: Chicken

<400> SEQUENCE: 1
gcgggggaac atgaatttct gaaaaccctc acacgccgcc cgtctgcgct cggctctccg      60
ggacggcgct caccatgagg ctcatccccg caggtgtcgt gcccttcgtg gccctgctgc     120
tgctgcagag gaggccggtg tccggcgggc gctgctggg gacgagctct gcgtgtccca     180
ccaacgggct gtgccgggcc aatgtcctgg agcagaccccg caggcaggtc gcactgctca     240
acgccaccgc gcaggacctc ttcagcctct acttgaagtg ccagggagag ccgttcagca     300
gcgagagcga ccgcctctgc agccccagtg gcatcttctt cccccccttc cacgtcaacc     360
ggaccaccga gaggaaggag gtgatggtgg ccatgtacaa gctcttcgcc ttcctcaacg     420
cctcactggg gaacatcacc cgcgaccagg aggagctcaa ccccatggcc aaggagctcc     480
tcaaccgcct ccacaacacc accaaaacca cgcggggcct catctccaac ctcacctgcc     540
tgctctgcaa gcactacaac atcttccagg tggacgtgag ctacggggag agcagcaagg     600
acaagagcgc cttcaagaag aagcagcagg gctgccaggt gctcaggaag tacgtgcagg     660
tcatcgccca ggctgctcgt gtcctcctac ctcacctcag ccccgcgtga gccccggccc     720
ccgcgccacg ctaccaccgg gacagcggac atctccttgc acccgtctca gagatgggca     780
cggcgaggc                                                             789

<210> SEQ ID NO 2
<211> LENGTH: 211
<212> TYPE: PRT
<213> ORGANISM: Chicken

<400> SEQUENCE: 2

Met Arg Leu Ile Pro Ala Gly Val Val Pro Phe Val Ala Leu Leu Leu
 1               5                  10                  15

Leu Gln Arg Arg Pro Val Ser Gly Arg Ala Leu Leu Gly Thr Ser Ser
                20                  25                  30

Ala Cys Pro Thr Asn Gly Leu Cys Arg Ala Asn Val Leu Glu Gln Thr
            35                  40                  45

Arg Arg Gln Val Ala Leu Leu Asn Ala Thr Ala Gln Asp Leu Phe Ser
        50                  55                  60

Leu Tyr Leu Lys Cys Gln Gly Glu Pro Phe Ser Ser Glu Ser Asp Arg
 65                 70                  75                  80

Leu Cys Ser Pro Ser Gly Ile Phe Phe Pro Phe His Val Asn Arg
                85                  90                  95
```

Thr Thr Glu Arg Lys Glu Val Met Val Ala Met Tyr Lys Leu Phe Ala
            100                 105                 110

Phe Leu Asn Ala Ser Leu Gly Asn Ile Thr Arg Asp Gln Glu Glu Leu
        115                 120                 125

Asn Pro Met Ala Lys Glu Leu Leu Asn Arg Leu His Asn Thr Thr Lys
    130                 135                 140

Thr Thr Arg Gly Leu Ile Ser Asn Leu Thr Cys Leu Leu Cys Lys His
145                 150                 155                 160

Tyr Asn Ile Phe Gln Val Asp Val Ser Tyr Gly Glu Ser Ser Lys Asp
                165                 170                 175

Lys Ser Ala Phe Lys Lys Gln Gln Gly Cys Gln Val Leu Arg Lys
            180                 185                 190

Tyr Val Gln Val Ile Ala Gln Ala Arg Val Leu Leu Pro His Leu
        195                 200                 205

Ser Pro Ala
    210

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
agagccgttc agcagcgaga gc                                              22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
gcctcgccgt gcccatctct ga                                              22

<210> SEQ ID NO 5
<211> LENGTH: 259
<212> TYPE: DNA
<213> ORGANISM: Chicken

<400> SEQUENCE: 5
acaagctctt cgccttcctc aacgcctcac tggggaacat caccgcgac caggaggagc      60 tcaaccccat ggccaaggag ctcctcaacc gcctccacaa caccaccaaa accacgcggg    120
gcctcatctc caacctcacc tgcctgctct gcaagcacta acatcttc caggtggacg    180 tgagctacgg ggagagcagc aaggacaaga gcgccttcaa gaagaagcag cagggctgcc    240
aggtgctcag gaagtacct                                                 259

<210> SEQ ID NO 6
<211> LENGTH: 201
<212> TYPE: PRT
<213> ORGANISM: Homo Sapien

<400> SEQUENCE: 6

Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala

```
                    20                  25                  30
Thr Cys Ala Ile Arg His Pro Cys His Asn Asn Leu Met Gln Ile Arg
                35                  40                  45

Ser Gln Leu Ala Gln Leu Asn Gly Ser Ala Asn Ala Leu Phe Ile Leu
 50                  55                  60

Tyr Tyr Thr Ala Gln Gly Glu Pro Phe Pro Asn Asn LeU Asp Lys Leu
 65                  70                  75                  80

Cys Gly Pro Asn Val Thr Asp Phe Pro Phe His Ala Asn Gly Thr
                85                  90                  95

Glu Lys Ala Lys Leu Val Glu Leu Tyr Arg Ile Val Val Tyr Leu Gly
                100                 105                 110

Thr Ser Leu Gly Asn Ile Thr Arg Asp Gln Lys Ile Leu Asn Pro Ser
                115                 120                 125

Ala Leu Ser LeU His Ser Lys Leu Asn Ala Thr Ala Asp Ile Leu Arg
                130                 135                 140

Gly Leu Leu Ser Asn Val Leu Cys Arg Leu Cys Ser Lys Tyr His Val
 145                 150                 155                 160

Gly His Val Asp Val Thr Tyr Gly Pro Asp Thr Ser Gly Lys Asp Val
                165                 170                 175

Phe Gln Lys Lys Lys Leu Gly Cys Gln Leu Leu Gly Lys Tyr Lys Gln
                180                 185                 190

Ile Ile Ala Val Leu Ala Gln Ala Phe
                195                 200

<210> SEQ ID NO 7
<211> LENGTH: 203
<212> TYPE: PRT
<213> ORGANISM: Mouse

<400> SEQUENCE: 7

Met Lys Val Leu Ala Ala Gly Ile Val Pro Leu Leu Leu Val Leu
 1               5                   10                  15

His Trp LYS His Gly Ala Gly Ser Pro Leu Pro Ile Thr Pro Val Asn
                20                  25                  30

Ala Thr Cys Ala Arg Ile His Pro Cys His Gly Asn Leu Met Asn Gln
                35                  40                  45

Ile Lys Asn Gln Leu Ala Gln Leu Asn Gly Ser Ala Asn Ala Leu Phe
                50                  55                  60

Ile Ser Tyr Tyr Thr Ala Gln Gly Glu Pro Phe Pro Asn Asn Val Glu
 65                  70                  75                  80

Lys Leu Cys Ala Pro Asn Met Thr Asp Phe Pro Ser Phe His Gly Asn
                85                  90                  95

Gly Thr Glu Lys Thr Lys Leu Val Glu Leu Tyr Arg Met Val Ala Tyr
                100                 105                 110

Leu Ser Ala Ser Leu Thr Asn Ile Thr Arg Asp Gln Lys Val Leu Asn
                115                 120                 125

Pro Thr Ala Val Ser Leu Gln Val Lys Leu Asn Ala Thr Ile Asp Val
                130                 135                 140

Met Arg Gly Leu Leu Ser Asn Val Leu Cys Arg Leu Cys Asn Lys Tyr
 145                 150                 155                 160

Arg Val Gly His Val Asp Val Pro Pro Val Pro Asp His Ser Asp Lys
                165                 170                 175
```

```
-continued

Glu Ala Phe Gln Arg Lys Lys Leu Gly Cys Gln Leu Leu Gly Thr Tyr
            180                 185                 190

Lys Gln Val Ile Ser Val Val Val Gln Ala Phe
        195                 200
```